United States Patent
Gennari et al.

(10) Patent No.: US 9,962,349 B2
(45) Date of Patent: May 8, 2018

(54) DERMAL THERAPEUTIC SYSTEM WITH HIGH ADHESIVITY

(71) Applicant: FIDIA FARMACEUTICI S.P.A., Abano Terme (PD) (IT)

(72) Inventors: Giovanni Gennari, Montegrotto Terme (IT); Anna Maria Zanellato, Bovolenta (IT); Patrizia Santi, Salsomaggiore Terme (IT); Cristina Padula, Parma (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days. days.

(21) Appl. No.: 15/519,388

(22) PCT Filed: Oct. 15, 2015

(86) PCT No.: PCT/IB2015/057913
§ 371 (c)(1),
(2) Date: Apr. 14, 2017

(87) PCT Pub. No.: WO2016/059583
PCT Pub. Date: Apr. 21, 2016

(65) Prior Publication Data
US 2017/0231936 A1    Aug. 17, 2017

(30) Foreign Application Priority Data
Oct. 17, 2014   (IT) .............................. MI2014A1803

(51) Int. Cl.
| A61K 31/196 | (2006.01) |
| A61K 47/10 | (2017.01) |
| A61K 47/12 | (2006.01) |
| A61K 47/22 | (2006.01) |
| A61K 9/70 | (2006.01) |

(52) U.S. Cl.
CPC .......... *A61K 31/196* (2013.01); *A61K 9/7061* (2013.01); *A61K 47/10* (2013.01); *A61K 47/12* (2013.01); *A61K 47/22* (2013.01)

(58) Field of Classification Search
CPC ...... A61K 31/196; A61K 47/10; A61K 47/12; A61K 47/22; A61K 9/7061
See application file for complete search history.

(56) References Cited

U.S. PATENT DOCUMENTS

| 6,193,996 B1 * | 2/2001 | Effing | A61K 9/7061 424/448 |
| 7,560,121 B1 | 7/2009 | Bracht et al. | |
| 2004/0146548 A1 * | 7/2004 | Takada | A61K 9/7053 424/449 |
| 2011/0268785 A1 | 11/2011 | Wen et al. | |

FOREIGN PATENT DOCUMENTS

| EP | 1 400 240 A1 | 3/2004 |
| WO | 01/28531 A1 | 4/2001 |
| WO | WO 2009/088142 A1 | 7/2009 |
| WO | WO 2010/130468 A1 | 11/2010 |
| WO | WO 2013/010737 A1 | 1/2013 |
| WO | WO 2014/012653 A1 | 1/2014 |

OTHER PUBLICATIONS

International Search Report for PCT/IB2015/057913 (PCT/ISA/210) dated Jan. 28, 2016.
Written Opinion of the International Searching Authority for PCT/IB2015/057913 (PCT/ISA/237) dated Jan. 28, 2016.

\* cited by examiner

*Primary Examiner* — Alma Pipic
(74) *Attorney, Agent, or Firm* — Birch, Stewart, Kolasch & Birch, LLP

(57) ABSTRACT

The present invention relates to a high adhesion dermal therapeutic system comprising an adhesive polymeric matrix with a salt of Diclofenac.

16 Claims, No Drawings

DERMAL THERAPEUTIC SYSTEM WITH HIGH ADHESIVITY

The present invention relates to a high adhesion dermal therapeutic system.

In general, a dermal therapeutic system comprises a polymeric matrix which acts as an adhesive layer and as a container of the active principle to be released. Furthermore, dermal therapeutic systems (or "medicated plasters" according to European Pharmacopoeia) are medical adhesive plasters which are applied to the skin to carry the drug topically to the application area, where they exert their therapeutic activity (locally). The active principle does not penetrate the bloodstream through the skin, or only in a limited quantity, which does not allow the active principle to exert its systemic action. Consequently, the administration of an active principle through a dermal therapeutic system or medicated plaster can be correctly defined as being a topical administration for local use.

In particular, the polymeric matrix must be able to dissolve the active principle in the desired concentrations, it must not chemically interact with the active principle, degrading it or changing its nature, it must allow its release, it must not cause irritation at the application site, it must have an adhesiveness which is such as to allow adhesion on the skin for the time necessary for the duration of the treatment.

The adhesion must, in fact, allow a close contact between the dermal therapeutic system and the outer layer of the skin for a time ranging from a few hours to a few days approximately, but at the same time, the dermal therapeutic system must be able to be removed at any moment without causing painful sensations and/or irritation to the skin.

Adhesive polymeric matrixes are known in the state of the art, prepared starting from a solution of adhesive polymers also defined as "Pressure Sensitive Adhesive (PSA) material".

In particular, the use of acrylic or methacrylic polymers is known, preferably having a glass transition temperature (Tg) lower than room temperature (or the temperature of use), having a soft consistency and therefore generally not requiring the presence of plasticizers. Polymers having a Tg<room T are commercialized dissolved in organic solvents.

An example of adhesive polymeric matrixes comprising acrylic or methacrylic polymers with a Tg<room T is described in EP1784169 and in WO 2010/130468. In this document, relating to transdermal polymeric matrixes, the polymers used are copolymers of acrylic acid and its acrylic and/or methacrylic esters, containing acid functions along the polymeric chain, wherein the free carboxyl groups are salified with compatible organic or inorganic bases. The polymeric matrixes of EP'169 and WO'468 use copolymers having a percentage of free carboxyl groups within the range of 0.1-15%, salified with bases selected from hydroxides, from alkaline, alkaline-earth or transition metals carbonates or bicarbonates, or from ammonia, methyl-acrylate ammonium copolymers, ethylenediamine, lysine.

An objective of the present invention is to find a dermal therapeutic system which overcomes the drawbacks of the state of the art (such as, for example, limited adhesion), in particular a dermal therapeutic system characterized by a high stability both with time and at different temperatures, and a dermal release profile of the active principle Diclofenac.

A further objective of the present invention is to find a therapeutic dermal system which allows close contact between the dermal therapeutic system and the outer layer of the skin for a time ranging from a few hours to about a few days and which at the same time, can be removed at any moment without causing painful sensations and/or irritation to the skin. This system ensures the skin release of the active principle Diclofenac, in a therapeutic amount within 12-24 hours from its dermal application.

The object of the present invention therefore relates to a dermal therapeutic system which comprises an adhesive polymeric matrix comprising
- an acrylate-vinyl acetate copolymer having a Tg lower than 0° C., preferably self-curing, containing free hydroxyl groups, said acrylate-vinyl acetate copolymer being present in a percentage ranging from 45 to 65% by weight with respect to the total dry weight of the adhesive polymeric matrix and a basic butylated methacrylate copolymer, said methacrylate copolymer being present in a percentage ranging from 5 to 20% by weight with respect to the total dry weight of the adhesive polymeric matrix, as adhesive components,
- an organic or inorganic acid in a percentage ranging from 0.5 to 3.5% by weight with respect to the total dry weight of the adhesive polymeric matrix, as stabilizer,
- a salt of diclofenac in a percentage ranging from 8 to 20% by weight with respect to the total dry weight of the adhesive polymeric matrix, as active principle,
- the complement to 100 consisting of pharmaceutically acceptable excipients and/or additives, such as, for example, adhesion modulators.

The system according to the present invention therefore comprises two different polymers associated in such a proportion as to ensure the preparation of a highly adhesive, stable and therapeutically efficient dermal system.

The Applicant has surprisingly found that only the association (according to specific values) of an acrylate-vinyl acetate copolymer containing hydroxyl groups, but without acid carboxyl functions, with the above-mentioned basic butylated methacrylate copolymer as adhesive components, with adhesion modulators and with the organic or inorganic acid, guarantees the preparation of a highly adhesive and effective therapeutic system in the constant release, at a dermal level, of diclofenac within 12-24 hours from skin application.

The acrylate-vinyl acetate copolymer having a Tg lower than 0° C., non-curing or self-curing, which contains free hydroxyl groups, does not have free carboxyl groups. Said copolymer is obtained from variable percentages of two or more monomers selected from a group comprising
- 2-ethylhexyl-acrylate
- 2-methyl-acrylate
- 2-hydroxyethyl-acrylate
- 2-oxyranylmethyl-methacrylate
- 1-butanol titanium salt and
- ethenyl acetate or vinyl acetate.

The acrylate-vinyl acetate copolymer of the adhesive polymeric matrix of the dermal therapeutic system according to the present invention is preferably selected from the copolymer known with the trade-name of Duro-Tak® 387-2287/87-2287 (non-curing PSA) (National Starch, Henkel, for example) and the copolymer known with the trade-name of Duro-Tak® 387-2516/87-2516 (self-curing PSA) (National Starch, Henkel, for example); the acrylate-vinyl acetate copolymer Duro-Tak® 387-2516/87-2516 is preferred.

The copolymer Duro-Tak® 387-2287/87-2287 is a non-curing acrylate-vinyl acetate copolymer having a Tg lower than 0° C., containing free hydroxyl groups and without free carboxyl groups, with a percentage of solids equal to 50.5% by weight, and a viscosity equal to 18,000 (mPa·s).

The copolymer Duro-Tak® 387-2516/87-2516 is a self-curing acrylate-vinyl acetate copolymer having a Tg lower than 0° C., containing free hydroxyl groups and without free carboxyl groups, with a percentage of solids equal to 41.5% by weight, and a viscosity equal to 4,350 (mPa·s).

The acrylate-vinyl acetate copolymer is preferably present in a percentage ranging from 50 to 60%, even more preferably from 53 to 58% by weight with respect to the total dry weight of the adhesive polymeric matrix.

The basic butylated methacrylate copolymer of the adhesive polymeric matrix of the dermal therapeutic system according to the present invention is preferably the copolymer having the trade-name of Eudragit® E100 (Rohm Pharma), normally used as film coating of solid oral formulations.

This is, more precisely, a cationic polymer and specifically a dimethylaminoethyl methacrylate copolymer having the following formula:

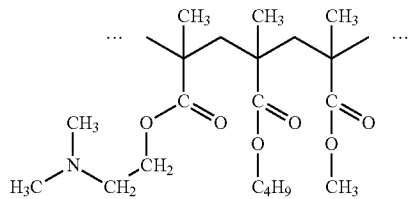

The basic butylated methacrylate copolymer is preferably present in a percentage ranging from 6 to 16%, even more preferably from 9 to 13% by weight with respect to the total adhesive polymeric matrix.

The active principle present in the polymeric matrix of the dermal therapeutic system according to the present invention is a salt of Diclofenac selected from the salts of alkaline metals, such as sodium or potassium salt, or the Diclofenac is salified with hydroxyethylpyrrolidine or it is a diethylammonium salt.

The Diclofenac salt is preferably sodium salt or diethylammonium salt, preferably in a percentage ranging from 10 to 20%, even more preferably from 12 to 16% by weight with respect to the total dry weight of the adhesive polymeric matrix.

The polymeric matrix of the dermal therapeutic system according to the present invention also comprises organic or inorganic acids, as stabilizers of the matrix.

The inorganic acid is preferably hydrochloric acid, whereas the organic acid is selected from mono-, di- or tri-carboxylic organic acids, and is preferably selected from citric acid, succinic acid, lactic acid, maleic acid, fumaric acid, salicylic acid, and acetic acid, and is even more preferably citric acid monohydrate, in a percentage ranging from 0.5 to 3.5%, preferably from 0.8 to 2.5%, even more preferably from 1 to 2% by weight with respect to the total dry weight of the adhesive polymeric matrix.

The adhesive polymeric matrix can also contain skin-soothing products, preservatives, moisturizers, adhesion modulators, etc. as excipients and/or pharmaceutically acceptable additives.

The polymeric matrix of the dermal therapeutic system according to the present invention preferably comprises, as adhesion modulators, polyethylene glycol (12 moles) stearate and/or sorbitan oleate, in a total percentage ranging from 10 to 30%, preferably from 12 to 25%, even more preferably from 15 to 20% by weight with respect to the total dry weight of the adhesive polymeric matrix.

A preferred formulation of the adhesive polymeric matrix of the dermal therapeutic system according to the present invention consists of
  56% by weight with respect to the total dry weight of the adhesive polymeric matrix, of Duro-Tak 387-2516/87-2516;
  11.1% by weight with respect to the total dry weight of the adhesive polymeric matrix, of Eudragit E100;
  13.4% by weight with respect to the total dry weight of the adhesive polymeric matrix, of sodium Diclofenac;
  13.4% by weight with respect to the total dry weight of the adhesive polymeric matrix, of polyethylene glycol (12 moles) stearate;
  4.5% by weight with respect to the total dry weight of the adhesive polymeric matrix, of sorbitan oleate;
  1.6% by weight with respect to the total dry weight of the adhesive polymeric matrix, of citric acid monohydrate.

A further preferred formulation of the adhesive polymeric matrix of the dermal therapeutic system according to the present invention consists of
  54.8% by weight with respect to the total dry weight of the adhesive polymeric matrix, of Duro-Tak 387-2516/87-2516;
  10.8% by weight with respect to the total dry weight of the adhesive polymeric matrix, of Eudragit E100;
  15.3% by weight with respect to the total dry weight of the adhesive polymeric matrix, of Diclofenac diethylammonium salt;
  13.1% by weight with respect to the total dry weight of the adhesive polymeric matrix, of polyethylene glycol (12 moles) stearate;
  4.4% by weight with respect to the total dry weight of the adhesive polymeric matrix, of sorbitan oleate;
  1.6% by weight with respect to the total dry weight of the adhesive polymeric matrix, of citric acid monohydrate.

The layer consisting of the adhesive polymeric matrix has a thickness ranging from 50 to 500 micron, preferably from 100 to 350 micron, and even more preferably has a thickness of 300 micron.

The dermal therapeutic system according to the present invention has the definite advantage of having a particularly high adhesion capacity, much higher than that of analogous products on the market, which allows an optimal period of use/application, stable with time, also at different temperatures.

The dermal therapeutic system according to the present invention also comprises a backing layer of the adhesive polymeric matrix which has an important role in the properties of use of the dermal system which is often applied in articulation areas and therefore requires a high degree of flexibility. Different types of materials can therefore be used, such as nonwoven fabric, foams, films and fabrics. In order to have a better tolerability of the dermal therapeutic system, it is important for the material used to also have a good permeability to steam. A nonwoven fabric of 100% polyester has been found as an optimum solution.

The dermal therapeutic system according to the present invention also comprises a protective layer that can, for example, be a siliconized polyester film or a nonwoven polyester fabric, well known to skilled persons in the field or a mono-siliconated glassine paper, i.e. an extremely resistant, smooth and almost transparent, mono-siliconated, calendered cellulose paper.

The dermal therapeutic system according to the present invention can be produced in dimensions ranging from 20 to 300 cm², preferably from 100 to about 150 cm².

The dermal therapeutic system according to the present invention preferably comprises a backing layer impermeable to the active principle, an adhesive layer consisting of the adhesive polymeric membrane containing the active principle and a removable protective layer.

In its simplest form the dermal therapeutic system according to the present invention can be effected in a way known to skilled persons in the field and specifically by mixing a solution of the adhesive copolymers in a low-boiling solvent with the active principle, regularly applying the mixture on the removable protective layer, eliminating the solvent by evaporation and covering the resulting product with a support.

More specifically, the dermal therapeutic system according to the present invention comprises the following steps:
  mixing of the low-boiling solvents,
  addition of the basic butylated methacrylate copolymer and vigorous stirring until complete dissolution,
  addition of the Diclofenac salt and stirring,
  addition of water and vigorous stirring,
  addition in succession of the adhesion modulators, stabilizers of the matrix and possible other excipients, under vigorous stirring, possibly after heating to 40° C., until complete dissolution,
  addition of the acrylate-vinyl acetate copolymer and slow stirring until complete dissolution,
  application of the mixture regularly on the removable protective layer,
  elimination of the solvent in an oven,
  lamination of the resulting product on a support.

The process for the preparation of the adhesive polymeric matrix therefore comprises the formation of a solvent-based system to which a certain quantity of water is then added. The polymeric matrix, initially solvent-based, is thus transformed into a solvent/water based mixture in which the active principle completely dissolves.

The percentage of water ranges from 1 to 5% by weight with respect to the total wet weight of the adhesive polymeric matrix.

Experiments aimed at determining the adhesiveness of the dermal therapeutic system according to the present invention were carried out according to the following procedure with the use of a dynamometer:
the sample to be tested was prepared by applying an adhesive tape on the central part of the dermal therapeutic system in order to avoid stretching the nonwoven fabric during the experiment for measuring the adhesiveness. The procedure for testing the adhesiveness comprises the following steps:
  cutting the samples, for example with dimensions of 25 mm (width)×100 mm (length);
  applying the sample to the surface of the panel exerting a slight pressure;
  constructing an extension with the adhesive tape to be inserted in the upper clamp of the dynamometer;
  passing the steel roll backwards and forwards on the sample;
  allowing the sample to rest;
  fixing the panel in the lower clamp of the dynamometer and fixing the adhesive tape in the upper clamp;
  removing the sample from the panel at a certain rate (for example a rate of 300±30 mm/min);
  expressing the adhesion force in N/cm;
  repeating the test on at least three test-samples;
  the final adhesiveness value is the average of the resulting measurements.

The present invention is illustrated in greater detail in the following example.

EXAMPLE 1

Preparation of a Dermal Therapeutic System Containing Diclofenac Sodium Salt.

16.46 g of ethyl acetate were mixed under mechanical stirring with 16.70 g of isopropanol. 12.94 g (11.11% by weight with respect to the total dry weight of the adhesive polymeric matrix) of Eudragit E100 (dimethylaminoethyl methacrylate copolymer) were added to this mixture of solvents and the whole mixture was left under vigorous stirring at room temperature until complete dissolution. 15.58 g (13.37% by weight with respect to the total dry weight of the adhesive polymeric matrix) of sodium Diclofenac were then added under stirring and 7.99 g of water under vigorous stirring for about 5 minutes.

The mixture was then heated to 40° C. and 15.66 g (13.44% by weight with respect to the total dry weight of the adhesive polymeric matrix) of polyethylene glycol (12 moles) stearate (Cithrol 6MS) were subsequently added under vigorous stirring until complete dissolution. 5.27 g (4.52% by weight with respect to the total dry weight of the adhesive polymeric matrix) of sorbitan oleate (Span 80V) were then added under stirring until complete dissolution, followed by 1.9 g (1.63% by weight with respect to the total dry weight of the adhesive polymeric matrix) of citric acid monohydrate under stirring until complete dissolution, and finally 157.49 g (55.94% by weight with respect to the total dry weight of the adhesive polymeric matrix) of Duro-Tak 387-2516/87-2516 (acrylate-vinyl acetate copolymer having a Tg lower than 0° C., self-curing, which comprises free hydroxyl groups), having a solid content of 41.5% w/w, under slow stirring, until about 250 g of a homogeneous mass were obtained.

For preparing the layer of adhesive polymeric matrix, the mixture was spread on a siliconated glassine paper (80 g/m²) having a thickness of 300 microns, using a manual spreader. The solvents were removed in an air-circulation oven by heating to 60° C. for 40 minutes.

A lamination was then effected, using a 100% polyester nonwoven fabric as support.

EXAMPLE 2

Preparation of a Dermal Therapeutic System Containing Diclofenac Salified with Diethylammonium.

This system was prepared following the same procedure described in Example 1, but 17.8 g (i.e. 15.3% by weight with respect to the total dry weight of the adhesive polymeric matrix) of Diclofenac diethylammonium salt were added instead of the sodium salt. At the end of the preparation process, a lamination was effected using a 100% polyester nonwoven fabric as support.

Adhesiveness Tests In Vitro

Various adhesive matrixes were prepared for this purpose (as comparison) as described in Example 1, substituting PSA Duro-Tak 87/2516 with a PSA containing carboxyl groups.

Preparation of the Comparative Adhesive Matrix

The comparative adhesive matrix was prepared according to the same procedure described in Example 1, substituting Duro-Tak 387-2516/87-2516 with Duro-Tak 87/2852, i.e. using 157.49 g of an acrylate copolymer having a Tg lower than 0° C., cured, that comprises up to 7% of free carboxyl groups, having a solid content of 33.5% w/w. The addition was effected under slow stirring, until about 250 g of a homogeneous mass were obtained. At the end of the preparation process, a lamination was effected using a 100% polyester nonwoven fabric as support.

Adhesion on a Steel Support Expressed in N/cm

| Sample | Preservation conditions | Adhesiveness Time 0 | Adhesiveness 1 month | Adhesiveness 3 months |
|---|---|---|---|---|
| Example 1 | 25° C. ± 2° C./ | 12.02 N/cm | 9.3 N/cm | 7.8 N/cm |
| Example 1 | 40° C. ± 2° C./ | 12.02 N/cm | 7.4 N/cm | 6.7 N/cm |
| Comparative plaster (Duro-tak® 87-2852) | 25° C. ± 2° C./ | 6.1 N/cm | 5.8 N/cm | 2.9 N/cm |
| Comparative plaster (Duro-tak® 87-2852) | 40° C. ± 2° C./ | 6.1 N/cm | 4.9 N/cm | 2.3 N/cm |

The tests carried out according to the procedure described above show that the adhesiveness of the therapeutic system according to the present invention is approximately double with respect to the adhesiveness of the comparative plaster, at both 25° C. and at 40° C.

The particular combination of elements forming the formulation of the adhesive polymeric matrix of the therapeutic system according to the present invention thus allows a high adhesiveness to be obtained, which is stable with time also at different temperatures.

The invention claimed is:

1. A dermal therapeutic system which comprises an adhesive polymeric matrix comprising:
    56% by weight with respect to the total dry weight of the adhesive polymeric matrix, of a self-curing acrylate-vinyl acetate copolymer having a Tg lower than 0° C., containing free hydroxyl groups and without free carboxyl groups;
    11.1% by weight with respect to the total dry weight of the adhesive polymeric matrix, of a copolymer of dimethylaminoethyl methacrylate, butyl methacrylate, and methyl methacrylate;
    13.4% by weight with respect to the total dry weight of the adhesive polymeric matrix, of sodium Diclofenac;
    13.4% by weight with respect to the total dry weight of the adhesive polymeric matrix, of polyethylene glycol (12 moles) stearate;
    4.5% by weight with respect to the total dry weight of the adhesive polymeric matrix, of sorbitan oleate; and
    1.6% by weight with respect to the total dry weight of the adhesive polymeric matrix, of citric acid monohydrate.

2. A dermal therapeutic system which comprises an adhesive polymeric matrix comprising:
    54.8% by weight with respect to the total dry weight of the adhesive polymeric matrix, of a self-curing acrylate-vinyl acetate copolymer having a Tg lower than 0° C., containing free hydroxyl groups and without free carboxyl groups;
    10.8% by weight with respect to the total dry weight of the adhesive polymeric matrix, of a copolymer of dimethylaminoethyl methacrylate, butyl methacrylate, and methyl methacrylate;
    15.3% by weight with respect to the total dry weight of the adhesive polymeric matrix, of Diclofenac diethylammonium salt;
    13.1% by weight with respect to the total dry weight of the adhesive polymeric matrix, of polyethylene glycol (12 moles) stearate;
    4.4% by weight with respect to the total dry weight of the adhesive polymeric matrix, of sorbitan oleate; and
    1.6% by weight with respect to the total dry weight of the adhesive polymeric matrix, of citric acid monohydrate.

3. The dermal therapeutic system according to claim 1, wherein the adhesive polymeric matrix has a thickness ranging from 50 to 500 microns.

4. The dermal therapeutic system according to claim 1, further comprising a backing layer and a protective layer.

5. The dermal therapeutic system according to claim 1, having a surface ranging from 20 to 300 cm².

6. The dermal therapeutic system according to claim 3, wherein the adhesive polymeric matrix has a thickness ranging from 100 to 350 microns.

7. The dermal therapeutic system according to claim 3, wherein the adhesive polymeric matrix has a thickness equal to about 300 micron.

8. The dermal therapeutic system according to claim 4, wherein the backing layer is a 100% polyester non-woven fabric and the protective layer is a siliconized polyester film, a non-woven polyester fabric, or a mono-siliconated glassine paper.

9. The dermal therapeutic system according to claim 5, having a surface ranging from 100 to about 150 cm².

10. The dermal therapeutic system according to claim 2, wherein the adhesive polymeric matrix has a thickness ranging from 50 to 500 microns.

11. The dermal therapeutic system according to claim 2, further comprising a backing layer and a protective layer.

12. The dermal therapeutic system according to claim 2, having a surface ranging from 20 to 300 cm².

13. The dermal therapeutic system according to claim 10, wherein the adhesive polymeric matrix has a thickness ranging from 100 to 350 microns.

14. The dermal therapeutic system according to claim 10, wherein the adhesive polymeric matrix has a thickness equal to about 300 micron.

15. The dermal therapeutic system according to claim 11, wherein the backing layer is a 100% polyester non-woven fabric and the protective layer is a siliconized polyester film, a non-woven polyester fabric, or a mono-siliconated glassine paper.

16. The dermal therapeutic system according to claim 12, having a surface ranging from 100 to about 150 cm².

* * * * *